(12) United States Patent
Fujikawa et al.

(10) Patent No.: US 7,837,895 B2
(45) Date of Patent: Nov. 23, 2010

(54) SUPERCOOLING PROMOTING AGENT (75) Inventors: Seizo Fujikawa, Sapporo (JP); Jun Kasuga, Sapporo (JP); Yasuyuki Hashidoko, Sapporo (JP); Keita Arakawa, Sapporo (JP); Yukiharu Fukushi, Sapporo (JP)

(73) Assignees: National University Corporation Hokkaido University, Hokkaido (JP); Olympus Corporation, Tokyo (JP)

( * ) Notice: Subject to any disclaimer, the term of this patent is extended or adjusted under 35 U.S.C. 154(b) by 2 days.

(21) Appl. No.: 12/309,332

(22) PCT Filed: Jul. 11, 2007

(86) PCT No.: PCT/JP2007/063784

§ 371 (c)(1),
(2), (4) Date: Jan. 14, 2009

(87) PCT Pub. No.: WO2008/007684

PCT Pub. Date: Jan. 17, 2008

(65) Prior Publication Data
US 2009/0302265 A1 Dec. 10, 2009

(30) Foreign Application Priority Data
Jul. 14, 2006 (JP) .............................. 2006-193468

(51) Int. Cl.
C09K 5/08 (2006.01)
C09K 3/00 (2006.01)
A01N 1/02 (2006.01)
C07H 17/07 (2006.01)

(52) U.S. Cl. .............................. 252/70; 252/71; 252/73; 435/1.3; 436/18; 536/8

(58) Field of Classification Search .................... 252/70, 252/71, 73; 536/8; 435/1.3; 436/18
See application file for complete search history.

(56) References Cited

U.S. PATENT DOCUMENTS

| | | | |
|---|---|---|---|
| 6,562,793 B2 * | 5/2003 | Wakabayashi et al. | 514/27 |
| 2006/0038159 A1 | 2/2006 | Fukutani et al. | |
| 2008/0171708 A1 * | 7/2008 | Begorod | 514/25 |

FOREIGN PATENT DOCUMENTS

| | | |
|---|---|---|
| EP | 1 262 535 | 12/2004 |
| JP | 2003-104818 A * | 4/2003 |
| JP | 2004-217545 A * | 8/2004 |
| WO | WO91/03935 | 4/1991 |
| WO | WO97/14785 | 4/1997 |
| WO | WO2004/074397 | 9/2004 |
| WO | WO2008/007684 | 1/2008 |

OTHER PUBLICATIONS

Chemical Abstract Accession No. 2006:72514, abstract of an article by Ahlenstiel et al entitled "Improved Cold Preservation of Kidney Tubular Cells by Means of Adding Bioflavonoids to Organ preservation Solutions", Transplantation 81(2), pp. 231-239, (Jan. 2006).*
Chemical Abstract Accession No. 2006:894298, abstract of Chinese Patent Specification No. CN 1698777 (Nov. 2005).*
Chemical Abstract Accession No. 2006:821455, abstract of Chinese Patent Specification No. CN 1813829 (Aug. 2006).*
"Plant ultralow storage manual" Ed. By Takao Niino, issued from National Institute of Agrobiological Sciences (2006), [no month].
"FLAVONOIDS Chemistry, Biochemistry and Applications" published in 2006 by CRC Press Taylor and Francis Group, Editor(s): Oyvind M. Andersen, University of Bergen, Norway; Kenneth R. Markham, Industrial Research Ltd., Lower Hutt, New Zealand, Chapter 13, pp. 749-802 (part 1 of 2), [no month].
"FLAVONOIDS Chemistry, Biochemistry and Applications" published in 2006 by CRC Press Taylor and Francis Group, Editor(s): Oyvind M. Andersen, University of Bergen, Norway; Kenneth R. Markham, Industrial Research Ltd., Lower Hutt, New Zealand, Chapter 13, pp. 803-856 (part 2 of 2), [no month].
"FLAVONOIDS Chemistry, Biochemistry and Applications" published in 2006 by CRC Press Taylor and Francis Group, Editor(s): Oyvind M. Andersen, University of Bergen, Norway; Kenneth R. Markham, Industrial Research Ltd., Lower Hutt, New Zealand, Chapter 15, pp. 917-959 (part 1 of 2), [no month].
"FLAVONOIDS Chemistry, Biochemistry and Applications" published in 2006 by CRC Press Taylor and Francis Group, Editor (s): Oyvind M. Andersen, University of Bergen, Norway; Kenneth R. Markham, Industrial Research Ltd., Lower Hutt, New Zealand, Chapter 15, pp. 960-1002 (part 2 of 2), [no month ].
Banri et al., "New antifreezing materials found from plants. Are antifreezing materials sharing of roles in antifreezing proteins (AFP) and phenolic compounds?" Kagaku to Seibutsu, vol. 37, No. 12, pp. 778-789 (1999), [no month].
Caple et al., "Biogenic effects in heterogeneous ice nucleation," CryoLetters, vol. 4 pp. 59-64 (1983), [no month].
Duman, "The inhibition of ice nucleators by insect antifreeze proteins is enhanced by glycerol and citrate," J. Comp. Physiol., vol. 172, pp. 163-168 (2002), [no month].
European Search Report corresponding to European Application No. 07790588.3-1221/2045306 PCT/JP2007063784 dated Nov. 26, 2009.

(Continued)

Primary Examiner—Anthony J Green
(74) Attorney, Agent, or Firm—Jenkins, Wilson, Taylor & Hunt, P.A.

(57) ABSTRACT

During the investigation of the mechanism that cellular water in woody plants growing in cold districts keeps liquid state at low temperature, the inventors have studied to identify the causative substances. As the results, the present inventors identified supercooling promoting agents in woody plants. The supercooling ability of identified flavonoid glycoside and synthesized flavonoid glycoside with similar structure was tested. It was found that the supercooling promoting agent comprising these flavonoid glycosides enables to stably supercool bulk water at low temperature for long-term. The aqueous solution containing the supercooling promoting agent of the present invention is useful to store biological materials at low temperature.

13 Claims, 7 Drawing Sheets

OTHER PUBLICATIONS

Gordon et al., "Protection by naringin and some other flavonoids of hepatocytic autophagy and endocytosis against inhibition by okadaic acid," The Journal of Biological Chemistry, vol. 270, No. 11, pp. 5830-5838 (1995), [no month].

Lee et al., "Total Synthesis of Kaempferol and Methylated Kaempferol Derivatives," J. Chin. Chem. Soc., vol. 48, pp. 201-206 (2001), [no month].

Kaoru et al., "Accumulation of anti-ice-nucleating substances in confier xylem," Cryobiology and Cryotechnology, vol. 51, No. 2, pp. 111-114 (2005), (Abstract), [no month].

Kawahara et al., "Identification of Compound in *Chamaecyparis taiwanensis* Inhibiting the Ice-Nucleating Activity of *Pseudomonas fluorescens* KUIN-1," Biosci. Biotechnol. Biochem., vol. 64, pp. 2651-2656 (2000), [no month].

Kawahara et al., "Identification of Compound in Spices Inhibition the Ice-nucleation Activity of *Erwinia uredobora* KUIN-3," J. Antibact. Antifung. Agents, vol. 24, 95-100 (1996)[no month].

McKown, "Cold responses of Arabidopsis mutants impaired in freezing tolerance," Journal of Experimental Botany, vol. 47, No. 305, pp. 1919-1925 (Dec. 1996).

Seizo et al., "Nonfreezing water. Searching for nonfreezing substance for water with supercooling/cryogenic property in tree xylem parenchymatous cell," Kagaku to Seibutsu, vol. 43, No. 5, pp. 280-282 (2005). Abstract Only, [no month].

Yamashita et al., "Identification of a novel anti-ice-nucleating polysaccharide from *Bacillus thuringiensis* YY529," Biosci. Biotechnol. Biochem., vol. 66, pp. 948-954 (2002), [no month].

* cited by examiner

- ◆ after excision
- —○— UV liquid, stored at 4 °C
- —◇— UV liquid +1% DMSO, stored at 4 °C
- —■— UV liquid +1% DMSO+0.01% K7G, stored at -5 °C
- —▲— UV liquid +1% DMSO+0.01% K7G, stored at -8 °C

Figure 9

SUPERCOOLING PROMOTING AGENT

FIELD OF THE INVENTION

The present invention relates to a supercooling promoting agent comprising flavonoid glycosides and an antifreezing and vitrification liquid containing the flavonoid glycosides.

BACKGROUND OF THE INVENTION

It is known that cellular water in growing woody plants in cold districts keep liquid state at low temperature. It is considered that water in xylem parenchyma cell is supercooled down to −40° C. due to the physical property of water, since water in xylem parenchyma cells is isolated from external environment as water droplets (Non-patent reference 1). In other words, cell walls surrounding xylem parenchyma cells act as barriers preventing dehydration from the cells and preventing penetration of extracellular ices into the cells when extracellular ices are generated, and thus intracellular water behaves as water droplets isolated from external environment and is supercooled.

Furthermore, it is suggested that phenol compounds contained in over-wintering plants function as antifreezing substances (Non-patent reference 2).

Still furthermore, it has been disclosed that flavonoids are used for freezing medium for culturing reproductive cells and the like (Patent reference 1) and for cooling liquid of internal combustion engine and the like as ingredients of antifreezing liquid (Patent reference 2).

Additionally, as for flavonoid glycosides as a supercooling promoting agent of the present invention, a various type thereof are present in plants including trees and in substances derived from living bodies as secondary metabolites (Non-patent reference 3).

Patent reference 1: Japanese Patent Application Public Disclosure No. 2000-500327 (WO97/14785)
Patent reference 2: International Publication WO2004/074397
Non-patent reference 1: Kagaku to Seibutsu, vol. 43, No. 5, 280-282 (2005)
Non-patent reference 2: Kagaku to Seibutsu, vol. 37, No. 12, 778-780 (1999)
Non-patent reference 3: "FLAVONOIDS Chemistry, Biochemistry and Applications" published in 2006 by CRC Press Taylor and Francis Group.

Problems to be Solved by the Invention

Although it is known that phenol compounds (flavonoids) may have a supercooling activity (Non-patent reference 2), it is not known that flavonoid glycosides have a supercooling promoting activity (Non-patent reference 3).

The present inventors have studied the mechanism by which cellular water in woody plants growing in cold districts keeps liquid state at low temperature and have studied to identify the causative agents. As the results, the present inventors succeeded in identifying the supercooling promoting agent in woody plants.

Means to Solve the Problems

The present inventors focused attention on xylem parenchyma cells, which keep stably supercooled state down to −40° C. for long-term such as several weeks in nature, and tried to isolate active ingredients from xylem of woody plants based on supercooling activity as an indicator. As the result, the inventors clarified that the causative substance to induce stable supercooling state in the cells was flavonoid glycosides. Furthermore, the inventors found that flavonoids glycosides with similar structure were significantly promotable supercooling ability of aqueous solution based on the elucidated structural property and accomplished the present invention.

In other words, the present invention is a supercooling promoting agent comprising a flavonoid glycoside represented by the following general formula:

[chemical formula 1]

wherein
at least one of $X^1$ to $X^4$ is a sugar residue in which a hydrogen is removed from the reducing end of hemiacetal hydroxyl group of monosaccharides or oligosaccharides and others are hydroxyl group or hydrogen atom; and
$R^1$ to $R^6$, which may be identical to or different from the other groups, are hydrogen atom, hydroxyl or methoxy group.

Moreover, the present invention is an antifreezing liquid prepared by dissolving the supercooling promoting agent in water or in an aqueous solution containing additives as usage, wherein the antifreezing liquid comprises equal to or more than 0.01 g/L of the supercooling promoting agent.

Still moreover, the present invention is a vitrification liquid comprising equal to or more than 0.01 g/L of the supercooling promoting agent in a vitrification solution, wherein the vitrification solution comprises 20-100% by volume of a cryoprotective agent alone or a combination thereof and the remainder is water or aqueous solution containing additives as usage.

Advantages of the Invention

The supercooling promoting agent of the present invention enables to supercool water by the addition of a flavonoid glycoside derived from living bodies or synthesized; and can be applied for low temperature storage, for controlling frozen state and the like.

The supercooling promoting agent of the present invention enables to lower freezing point of Water and substances containing water by about 15° C. from natural freezing point of water. The supercooling promoting agent enables to stably supercool bulk water at low temperature for long-term.

Furthermore, the supercooling promoting agent of the present invention generates nonfreezing liquid by mixing with water, wherein the nonfreezing liquid is usable at about −15° C. and usable for storing biological materials and the like at low temperature for long-term.

The supercooling promoting agent of the present invention enables to use as a freeze control agent, which regulates the size of frazil crystals by freezing water; aqueous solution of additives as usage; or additive dissolved in substance including water. Addition of the substance lowers freeze starting temperature due to supercooling and thus reduces the size of frazil crystals formed. Therefore, the solution containing the additive could be used as a freezing control agent, which changes the ice size variously, in case of freezing by changing the cooling rate, composition or concentration of additives.

Moreover, it is possible to lower the concentration of vitrification liquid by the addition of the supercooling promoting agent of the present invention to a vitrification liquid containing high concentration of cryoprotective agent. Lowering the concentration of vitrification liquid may reduce the toxicity caused by dipping in vitrification liquid, produce glass bodies efficiently at ultra-low temperature such as liquid nitrogen temperature, and enables to store biological materials in glass bodies at ultra-low temperature, wherein the biological materials have been difficult of vitric storage.

BRIEF DESCRIPTION OF THE DRAWINGS

FIG. 9A used vitrification liquid containing kaempferol-7-O— glucoside and FIG. 9B used that without kaempferol-7-O-glucoside. The horizontal axis shows the loading time (min) and the vertical axis shows viability (%).

DETAILED DESCRIPTION OF THE INVENTION

The supercooling promoting agent of the present invention, i.e. a flavonoid glycoside, is represented by the following formula:

[chemical formula 2]

wherein
at least one of $X^1$ to $X^4$ preferably $X^1$ and $X^2$, or $X^2$ and $X^4$, more preferably $X^1$ and $X^2$, most preferably $X^2$, is a sugar residue in which a hydrogen is removed from the reducing end of hemiacetal hydroxyl group of monosaccharides or oligosaccharides. Naturally, only those residues containing sugar residues bound to $X^1$ and $X^2$, or $X^2$ and $X^4$ by glycoside bonding are known. Together with the residues, those with glycosylated several synthesizable hydroxyl groups (such as $X^3$) are not excluded.

Additionally, a hemiacetal hydroxyl group is represented for example by a hydroxyl group bound to C1 carbon of the basic skeleton of the following monosaccharide and disaccharide:

[chemical formula 3]

The monosaccharide includes glucose, mannose and galactose; and oligosaccharide includes rutinose, raffinose and the like; and a sugar residue is preferably monosaccharide such as glucose, mannose and galactose.

$X^1$ to $X^4$ other than sugar residues are hydroxyl group or hydrogen atom; and preferably at least one of them is hydrogen atom, and more preferably $X^3$ is hydroxyl group and $X^4$ is hydrogen atom.

$R^1$ to $R^6$, which may be identical to or different from the other groups, are hydrogen atom, hydroxyl or methoxy group.

Among them, $R^1$ is preferably hydrogen atom or hydroxyl group, more preferably hydrogen atom.

$R^4$ is preferably hydrogen atom or methoxyl group, more preferably hydrogen atom. $R^2$, $R^3$, $R^5$ and $R^6$ are preferably hydrogen atom.

Since flavonoid glycosides of the present invention are contained in all kinds of living bodies such as woody plants, they might be isolated from the woody plants or substances derived from living bodies or might be synthesized.

As for the woody plants, it is considered that woody plants of cold districts contain the supercooling promoting agents in abundance and suitable to the present purpose. Such acicular tree includes, for example, *Larix kaempferi* (Japanese larch), *Thuja occidentalis* (white ceder), *Taxus cuspidata* (Japanese yew), *Cryptomeria japonica* (Japanese cedar), *Abies homolepis* (Nikko fir), *Abies sachalinensis* (Todo fir), *Picea jezoensis* (Yezo Spruce), *Picea glehnii* (Sakhalin Spruce), *Pinus parviflora* (Japanese white pine), *Pinus strobus* (white pine), *Pinus sylvestris* (Japanese red pine), *Pinus thunbergii* (Japanese black pine) and the like. Also, broad leaf tree includes *Betula platyphylla* var. *japonica* (white birch), *Populus sieboldii* (Japanese aspen), *Castanea crenata* (Japanese Chestnut), *Sorbus commixta* (Japanese Rowan), *Styrax obassia* (Fragrant snowbell), *Quercus crispula* (Japanese oak), *Ulmus davidiana* var. *japonica* (Japanese elm), *Cercidiphyllum japonicum* (Katsura tree) and the like. Said supercooling promoting agents are contained also in woody plants growing in regions other than cold districts regardless of the amount of the contents. Said flavonoid glycosides can be isolated from not only xylem including sap wood and heart wood of the tree species but also barks, winter buds and leaves. Moreover, although it is considered that the supercooling promoting agents are present in living cells (parenchyma cells), it is possible that the agents are present at extracellular portion. Additionally, the agents are stable and can be isolated from not only raw standing crop but also dead standing crop and timber stored for long-term.

The supercooling promoting agent of the present invention shows supercooling activity of temperature range between −0.1° C. and −15.0° C. The supercooling activity (or represented as inhibiting activity of ice nucleus formation) is the value measured by the following method. A buffer solution containing dead bacterial cells of ice nucleation active bacteria (Erwinia ananas) mixed with 0.5 mg/mL of a test sample is prepared. A large number of 2 μL droplets of the solution are put on a cupper plate, which is temperature-controllable. Then, the cupper plate is cooled at the rate of 0.2° C./min, the number of frozen droplets are counted macroscopically and the temperature, wherein 50% of droplets are frozen, is defined as freezing point. The supercooling activity is defined as the difference (° C.) between the freezing point of solution containing test sample and ice nucleation active bacteria, and that of solution containing only ice nucleation bacteria and buffer solution.

The supercooling promoting agent (or supercooling substance) is defined as the substance, which has supercooling activity far exceeding the concentration-dependent freezing point depression induced by adding low concentration (generally equal to or less than 1% by volume or by weight) of the substance to water.

Although general substances such as salts, sugars and sugar alcohols show increased supercooling activity of about two-fold of freezing point depression, supercooling promoting agents show supercooling activity of more than 10 times or some times more than 100 times.

The supercooling activity of the present flavonoid glycoside is superior to the activity of the following other so called supercooling substances.

1) The unidentified crude extract extracted from seeds of various plants (peach and others) shows supercooling activity of water in the temperature range between −2.6° C. and −8.1° C. (Caple et al., (1983) Cryoletters, 4, 59-64). However, the value was obtained under the condition that only silver iodide having low ice nucleation forming ability was used and the cooling rate was 1° C./min, which is far rapid than the cooling rate of the supercooling promoting agent of the present invention. Hence, the condition is apt to induce transient supercooling.

2) Eugenol extracted from clove and its allied substances show supercooling activity of water in the temperature range between −0.2° C. and −2.5° C. (Kawahara and Obata (1996) J. Antibact. Antifung. Agents, 24, 95-100). The concentration of additives is 1 mg/mL and the cooling rate was 1° C./min, which is far rapid than the cooling rate of the supercooling promoting agent of the present invention. Hence, the condition is apt to induce transient supercooling.

3) Hinokitiol and its allied substances show supercooling activity of water in the temperature range of between −0.4° C. and −2.1° C. (Kawahara et al., (2000) Biosci. Biotechnol. Biochem., 64, 2651-2656).

The concentration of additives is 10 mM and the cooling rate was 1° C./min, which is far rapid than the cooling rate of the supercooling promoting agent of the present invention. Hence, the condition is apt to induce transient supercooling.

4) Chitin polysaccharide with 130 kDa isolated from bacteria show supercooling activity of water in temperature range between −0° C. and −4.2° C. (Yamashita et al., (2002) Biosci. Biotechnol. Biochem., 66, 948-954). The concentration of additives is 50 μg/mL and the cooling rate was 1° C./min, which is far rapid than the cooling rate of the supercooling promoting agent of the present invention. Hence, the condition is apt to induce transient supercooling.

5) Various antifreeze proteins show supercooling activity of water at the maximum −7.8° C. (Duman (2002) J. Comp. Physiol., 172, 163-168). However, the concentration of added nonfreezing protein at the maximum supercooling promoting activity is not known and high concentration of citric acid (0.5 M) is added together with the proteins at the maximum activity. Only the antifreeze protein promotes supercooling of −1.2° C.

The supercooling promoting agent of the present invention comprises the flavonoid glycoside.

Said flavonoid glycoside is typically used for aqueous solution and can be used for antifreezing liquid, wherein the flavonoid is dissolved in water typically at equal to or more than 0.01 g/L, preferably between 0.01 and 30 g/L, more preferably between 0.01 and 10 g/L, still more preferably between 0.1 and 1.0 g/L.

Said antifreezing liquid is obtainable by dissolving flavonoid glycoside typically in water, which could be replaced with aqueous solution containing additives as usage. Said additives include, for example, ingredients of culture medium of animal and plant cells and ingredients of storage solution of biological materials. The concentration of additives in aqueous solution may be suitably determined as usage.

Furthermore, the antifreezing liquid may contain other supercooling promoting agents and cryoprotective agents. In the case of cryoprotective agents, a cryoprotective agent alone or a combination thereof may be included at the concentration range between 1 and 40% by volume, preferably between 1 and 20% by volume.

A cryoprotective agent is defined as a substance reducing freeze-induced damage by adding the substance to biological materials or aqueous solution dipped therewith. All of cryoprotective agents show an effect or a combination thereof selected from the effects including concentration-dependent freezing point depression, reduction of frazil ice formation, reduction of increase in salt concentration in freezing materials and promotion of vitrification Such cryoprotective agents include, for example, methanol, ethanol, acetamide, DMSO, formaldehyde, ethylene glycol, propylene glycol, glycerol, proline, glucose, sorbitol, sucrose, trehalose, polyethylene glycol, dextran 10-150, PVP, albmin, ficoll, HES and the like.

Such antifreezing liquid can keep liquid state down to about −15° C. for long-term (1 to 2 weeks) under the condition, wherein no cryoprotective agent is added, or additives such as cryoprotective agent are mixed at a concentration (less than about 1% by weight) with almost no effect to freezing point depression.

Although biological materials (plant or animal cells or tissues, eatable or ornamental fish and seafood, plant itself such as vegetable, or a part thereof) are usually stored in the antifreezing liquid less than about 5° C., long-term low temperature storage is possible without freezing by dipping the biological materials in the antifreezing liquid at less than 0° C., particularly between about 0° C. and −15° C.

Said antifreezing liquid enables to reduce the size of ice crystal by lowering the freeze starting temperature based on supercooling, and is usable as a freeze control agent of medications and foods prepared by freeze-drying by the use of only antifreezing liquid or by simultaneous use of cryoprotective agents. Isolates (crude extract and others) isolated from biological materials such as trees as well as the above substances are applicable similarly.

In contrast, liquid containing high concentration of the above cryoprotective agent is called as "vitrification liquid"; and water does not generate crystals even at ultra-low temperature (i.e., liquid nitrogen temperature) and becomes a glass body (amorphous ice) (Ed. by Takao Niino "Plant ultralow storage manual" issued from National Institute of Agrobiological Sciences, 2006).

Vitrification liquid is defined as solution, wherein the cryoprotective agents are contained by themselves or in combination thereof at the concentration between 20 and 100% by volume, preferably between 40 and 100% by volume, and the remainder is water. Solvent such as animal and plant cell culture medium could be used instead of the water.

For culture and storage of animal and plant cells, it is preferable to mix equal to or more than 30% by volume, particularly equal to or more than 40% by volume of water and culture medium of animal and plant cells. PVS2, the vitrification liquid most frequently used, comprises culture medium supplemented with 30% by volume of glycerol, 15% by volume of ethylene glycol, 15% by volume of DMSO and 0.4 M sucrose. The type and concentration of culture medium is suitably changed depending on culture and material to be stored.

In the present invention, the supercooling promoting agent (the above-described flavonoid glycoside) of the present invention is added typically equal to or more than 0.01 g/L, preferably between 0.01 and 30 g/L, more preferably between 0.01 and 10 g/L, further preferably between 0.1 and 1.0 g/L in the vitrification liquid.

The above-described glass body may maintain amorphous state at less than freezing point of vitrification liquid, for example at equal to or less than −15° C., particularly between at −60° C. and −273° C., for example at liquid nitrogen temperature (77K).

In the case of freeze preservation by vitrification, generally the material for storage is subjected to pre loading treatment for short term at room temperature or at temperature equal to or more than 0° C. The pretreatment leads to dehydration of moisture content in the materials by high concentration of vitrification liquid and concurrently replace moisture content in materials with vitrification liquid. Hence, moisture content in the materials is vitrified without forming ice crystals on sinking the materials in liquid nitrogen. When biological materials such as plants are sunk in vitrification liquid and are plunged into liquid nitrogen, moisture inside and outside of biological materials is changed to glass bodies (amorphous ices). Since vitrification state dose not induce damage by freezing, biological materials can be lead to freeze preservation in vitrification liquid at ultra-low temperature.

The present invention is illustrated in the following Examples, but these Examples are not intended to limit the scope of the present invention

EXAMPLE 1

Twigs are collected from *Cercidiphyllum japonicum* tree (Katsura tree) growing naturally at Sapporo area in Hokkaido. After the xylem tissues of Katsura tree are fractionated by a pencil sharpener, frozen in liquid nitrogen and ground to pieces as small as possible by the use of a mortar and a pestle. The obtained 3.7 Kg of ground products were soaked in 20 L of methanol for 2 weeks. The obtained crude extract was centrifuged at 14,000 G (Hitachi: HIMC CF15R), and the supernatant was recovered. The supernatant was dried and the dried material (93.8 g) was dissolved in 300 mL water. The aqueous suspension of the crude extract was centrifuged at 14,000 G at 20° C., and the supernatant was recovered. After the supernatant (300 mL) and 600 mL ethyl acetate were mixed, water-soluble fraction and ethyl acetate-soluble fraction were separated by the use of a separatory funnel and dried.

The supercooling activities of these samples were measured by the following methods. After a buffer solution (50 mM potassium phosphate buffer, pH 7.0) containing dead bacterial cells (Wako pure chemical industries Ltd.,) of ice nucleation active bacteria (*Erwinia ananas*) mixed with 0.5 mg/mL of a test sample, 2 µL droplets of the solution are put on a cupper plate, which is temperature-controllable. Then, the cupper plate is cooled at the rate of 0.2° C./min, the number of frozen droplets are counted macroscopically and the temperature, wherein 50% of droplets are frozen, is defined as freezing point. The difference (° C.) between the freezing point and that of the buffer solution was measured. Obtained supercooling activity was about −2° C. and about −4° C., respectively, for the water-soluble fraction and ethyl acetate-soluble fraction.

Figure 1:
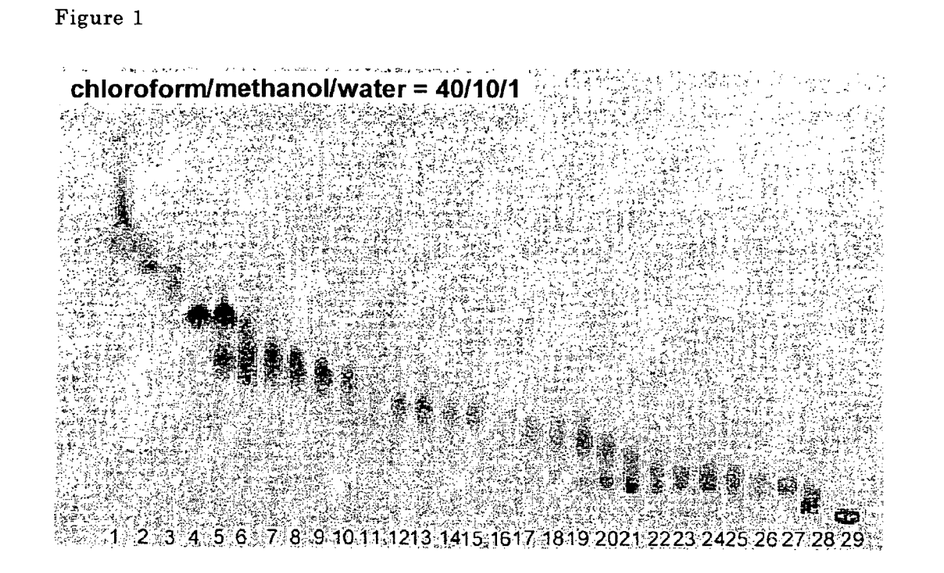
FIG. 1 shows the silica gel column chromatography of ethyl acetate-soluble fraction of isolates from *Cercidiphyllum japonicum* tree (Katsura tree).
Figure 2:
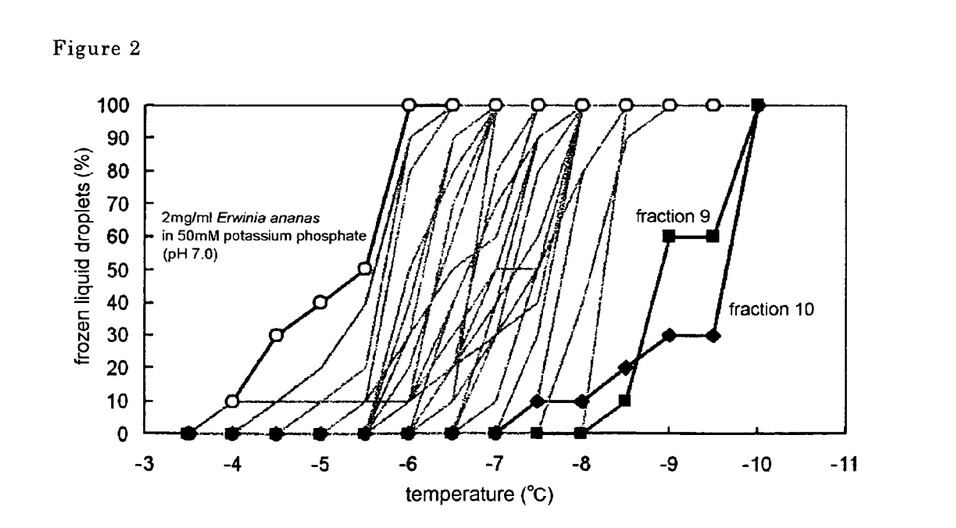
FIG. 2 shows the supercooling activity of silica gel column chromatography fractions. The horizontal axis shows the temperature of cupper plate loaded with liquid droplets and the vertical axis shows the percentage of frozen liquid droplets.

The dried ethyl acetate fraction, which showed the highest supercooling activity, was fractionated to about 30 fractions through a self-produced silica gel column chromatography by the use of "hexan-2-propanol-water" and "chloroform-methanol-water" as the eluent. The silica gel column chromatograph is shown in FIG. 1. Then, supercooling activity of the substance from each fraction was measured according to the similar method to the above-described one. As shown in FIG. 2, the fractions 9 and 10 show the maximum supercooling activity.

Figure 3:
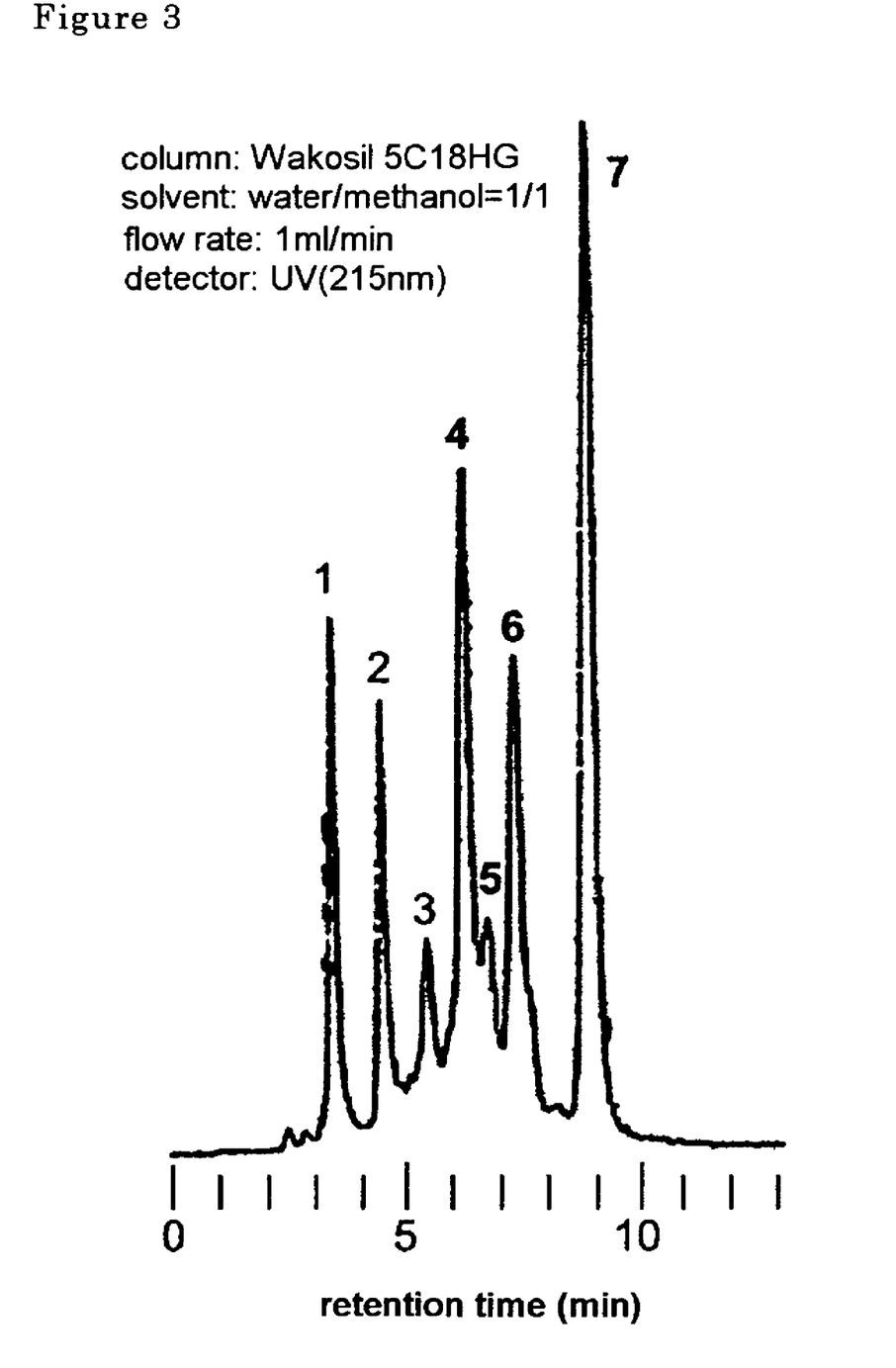
FIG. 3 shows the high performance liquid chromatography loaded with the above fractions number 9 and 10.

The above obtained fractions 9 and 10 were analyzed by high performance liquid chromatography (column: Wakosil 5C18HG, solvent: methanol:water=1:1, flow speed: 1 mL/min). As shown the result in FIG. 3, peaks (1 to 7), which show the presence of 7 substances, were obtained. Among these peaks, only peaks 4, 5, 6 and 7 showed supercooling activity (hereinafter, these substances are called as compound 1 to 4 (Cj4 to 7)), and the activities are −1.8° C. (compound 1), −7.7° C. (compound 2), −0.2° C. (compound 3) and −2.5° C. (compound 4), respectively.

For these 4 types of compounds, negative-HRFAB-MS analysis was performed by mass spectrometer (JMS-AX500: JEOL). The masses of these compounds were 463.0893 (Cj4), 447.0942 (Cj5), 477.1038 (Cj6) and 447.0958 (Cj7), respectively and these molecular formulas were expected as $C_{21}H_{20}O_{12}$ (Cj4), $C_{21}H_{20}O_{11}$ (Cj5), $C_{22}H_{22}O_{12}$ (Cj6) and $C_{21}H_{20}O_{11}$ (Cj7), respectively.

Furthermore, these compounds were acetylated and the reaction products were analyzed by high resolution nuclear magnetic resonance apparatus (BRUKER: AMX-500) on various types of one dimensional and two dimensional NMR spectra analysis. Acetylation reaction was performed according to the following procedures: about 10 mg of dried sample was dissolved in 200 mL of methanol, then was added with 2 mL of acetic anhydride and 1 mL of pyridine, and the mixture was kept at 70° C. for 1.5 hr. After the obtained acetylated derivatives were purified by preparative TLC, they were dissolved in chloroform-d, and were subjected to NMR spectrum analysis on $^1$H-NMR, $^{13}$C-COM, DEPT, $^1$H-$^1$H COSY, HMBC, HSQC.

Since all of the compounds showed characteristic UV spectra with absorption peaks at 250 to 270 nm and 300 to 380 nm, the compounds were expected to have flavonol backbone. $^1$H-NMR spectrum of each acetylated derivative is shown in FIG. 4 to 7.

Figure 4:
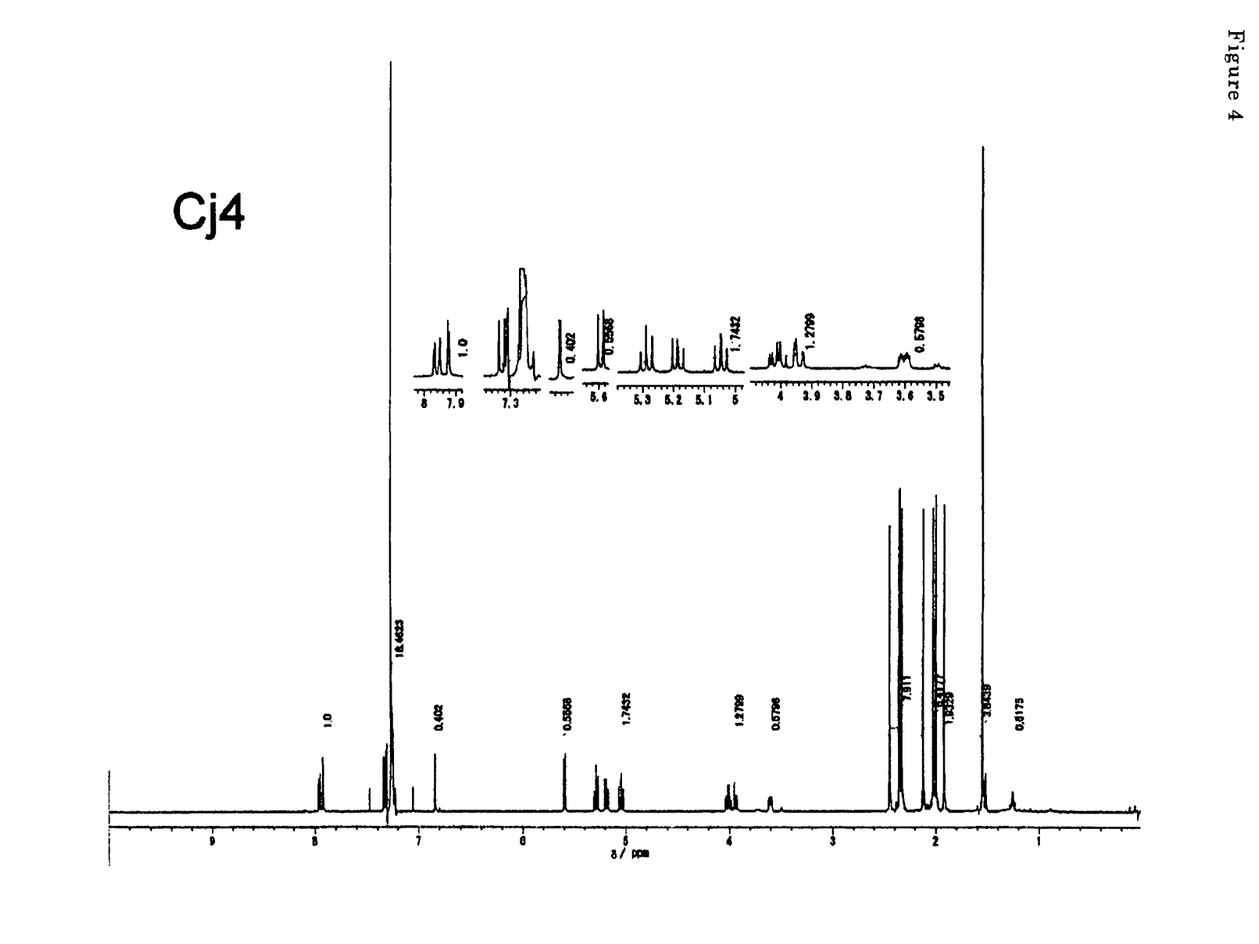
FIG. 4 shows the $^1$H-NMR spectrum of an acetylated derivative of compound 1.
Figure 5:
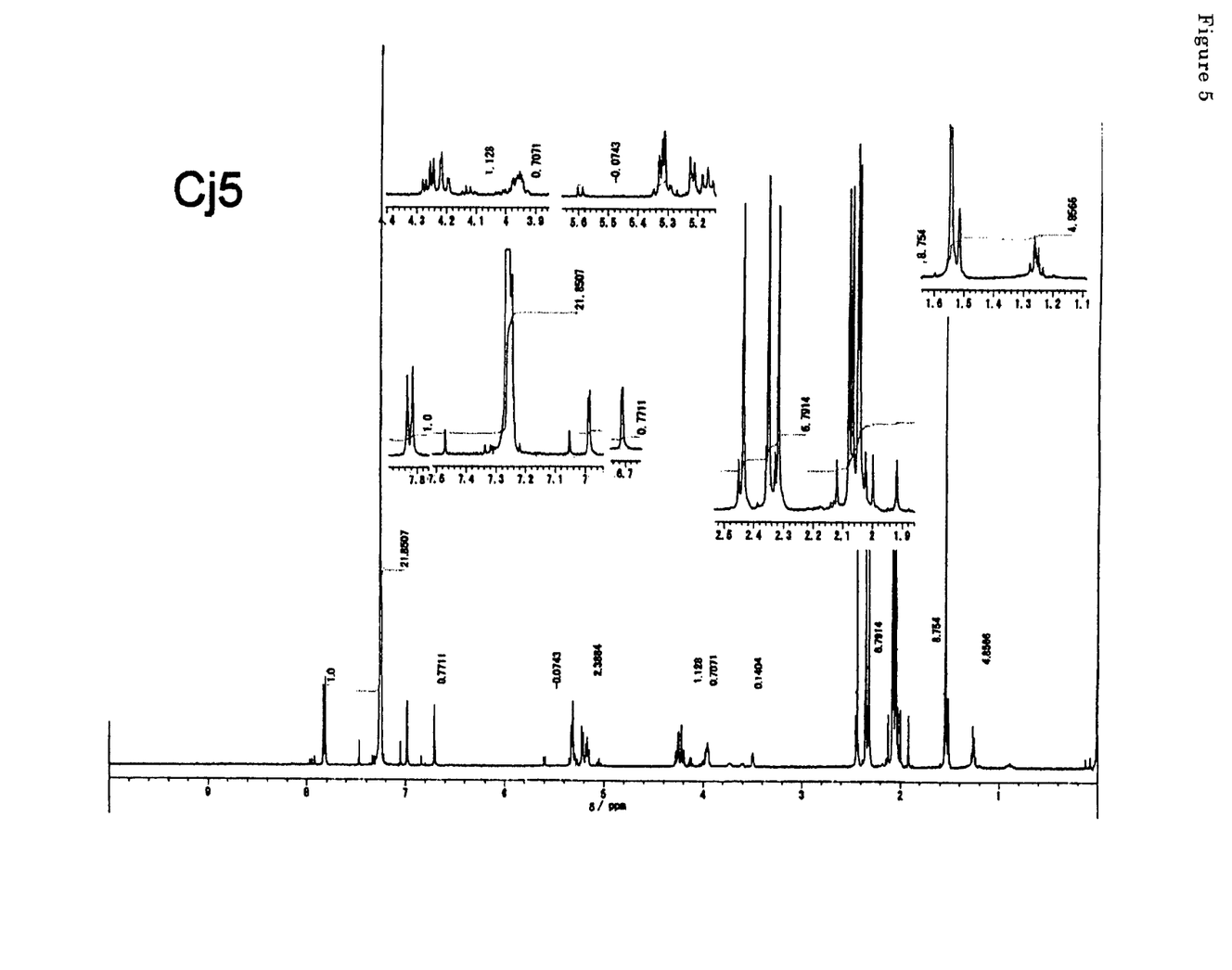
FIG. 5 shows the $^1$H-NMR spectrum of an acetylated derivative of compound 2.

When $^1$H-NMR spectrum of compound 1 (Cj4) is compared to that of compound 4 (Cj7), there are 8 signals (δ 1.92 to 2.45) attributed to acetyl group and signals (δ 7.33, 7.93, 7.96) attributed to hydrogen bound to 2', 5' and 6' positions of B ring in compound 1. Based on the result and HMBC correlation, compound 1 was identified as quercetin-3-O-β-glucoside (FIG. 4). $^1$H-NMR spectrum of an acetylated derivative of compound 2 (Cj5) shows 7 signals (δ 1.92 to 2.45) attributed to acetyl group similar to those of compound 4 (Cj7) and signals (δ 7.27, 7.84) attributed to hydrogen bound to 2', 3', 5' and 6' positions of B ring and 2 signals (δ 6.73, 7.01) attributed to hydrogen bound to aromatic ring. Additionally, $^1$H-NMR spectrum of an acetylated derivative of constituent sugar obtained from acetylated acid hydrolyzate of compound 2 was identical to that of acetylated glucose (FIG. 5). Since there is HMBC correlation between hydrogen at 1 position of constituent sugar and carbon at 7 position of aglycon, compound 2 was identified as kaempherol-7-O-β-glucoside.

Figure 6:
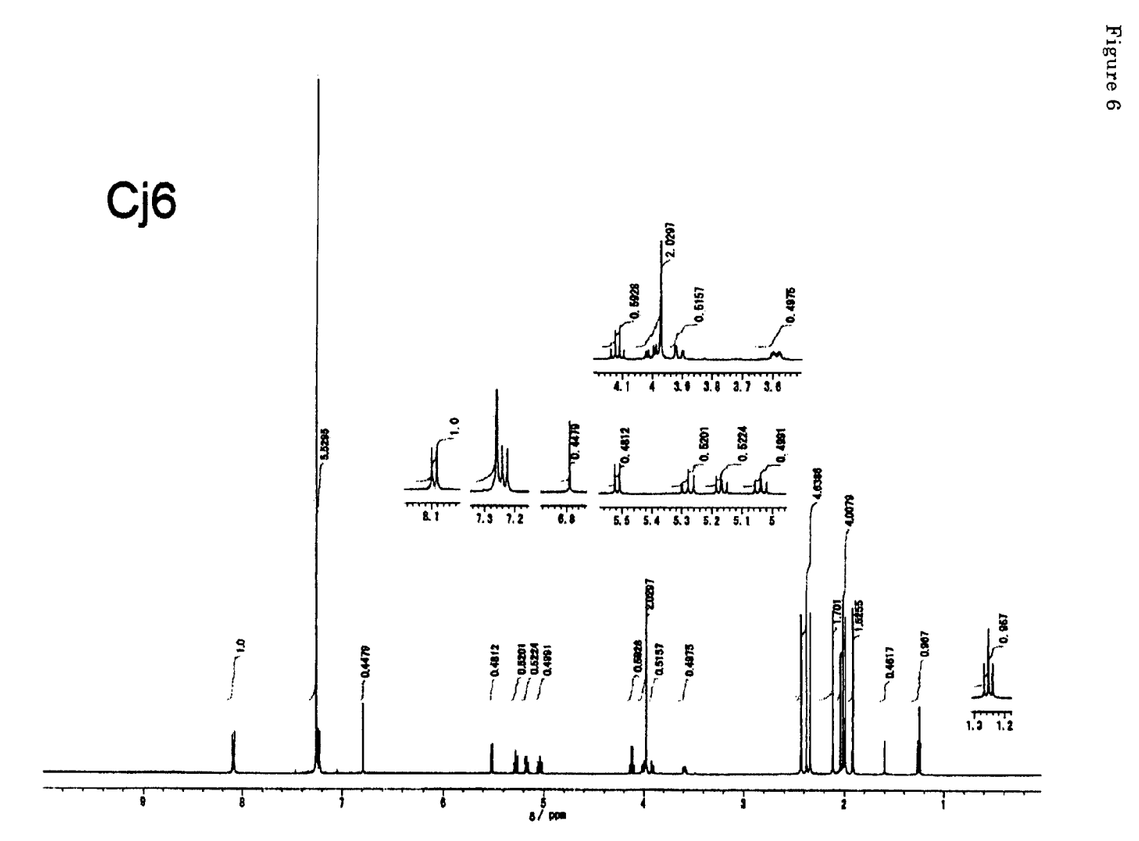
FIG. 6 shows the $^1$H-NMR spectrum of an acetylated derivative of compound 3.

When $^1$H-NMR spectrum of an acetylated derivative of compound 3 (Cj6) was compared to that of compound 4 (Cj7), there are single hydrogen (δ 6.79) bound to aromatic ring and a signal (δ 4.01) of methoxyl group in compound 3. Based on the result and HMBC correlation, compound 3 was identified as 8-methoxykaempferol-3-O-β-glucoside (FIG. 6).

Figure 7:
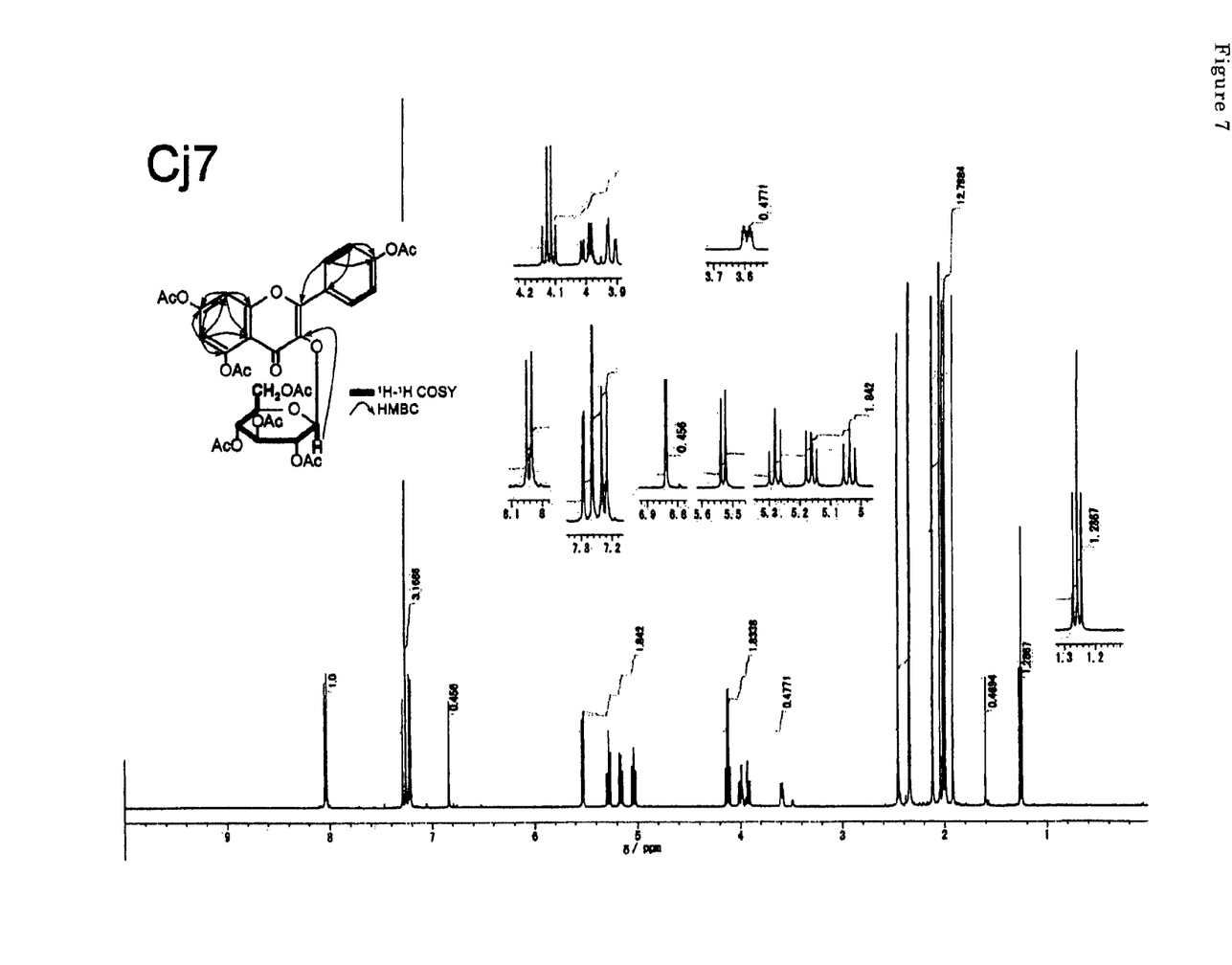
FIG. 7 shows the $^1$H-NMR spectrum of an acetylated derivative of compound 4.

$^1$H-NMR spectrum of an acetylated derivative of compound 4 (Cj7) shows 7 signals (δ 1.92-2.45) attributed to acetyl group, signal (δ 7.23, 8.04) attributed to hydrogen bound to 2', 3', 5' and 6' positions of B ring and 2 signals (δ 6.84, 7.30) attributed to hydrogen bound to aromatic ring. Moreover, presence of β-glucose residues (δ 3.60, 3.96, 5.04, 5.17, 5.28, 5.53) was confirmed. HMBC correlation was observed between hydrogen bound to anomeric carbon of glucose and carbon at 3 position of aglycon. Based on the above results, compound 4 was identified as kaempferol-3-O-β-glucoside (FIG. 7).

Based on these results on mass spectrometric and NMR spectrometric analysis, it was concluded that all these compounds are flavonoid glycoside, which is a glycoside with a glucose bound to aglycon, wherein the aglycon is any one of quercetin, kaempferol and 8-methoxykaempferol.

Namely, the isolated supercooling promoting agent is flavonoid glycoside represented by the following formula:

[chemical formula 4]

, wherein the number in the formula represents the number of the compound.

SYNTHETIC EXAMPLE 1

In the present synthetic example, compound 5 (Chrycin-7-O-β-D-glucopyranoside) was synthesized. Chrycin (Tokyo Chemical Industry, Ltd., Tokyo, Japan, 0.51 g (2.0 mmol)), 1.38 g (10 mmol) of $K_2CO_3$, 0.12 g (0.4 mmol) of benzyl-tributyl-ammoniumchloride and $CHCl_3$ (10 mmol) were stirred with a magnet, added with 1.61 g (3.8 mmol) of tetra-O-acetyl-α-D-glucopyranosilbromide (Kanto Chemical Co.), at room temperature and were refluxed with heating for 2 hr. Furthermore, the mixture was added with above described bromide (1.00 g (2.4 mmol)) and was kept refluxing with heating for 1 hr. After the reaction mixture was shaken with 20 mL of 2N hydrochloric acid, organic layer was separated and dried with $MgSO_4$. The residue obtained by concentration under reduced atmosphere was crystallized in hexane-ethanol, and 1.03 g of Chrycin 7-O-β-D-tetra-O—acetylglucopyranoside was obtained (yield 88%).

The analytical values of the product are shown as follows.

FAB-MS: m/z 585 (M+H$^+$, 57%), 331 (29), 255 (100). FAB-HR-MS: m/z 585.1599 (calc. for $C_{29}H_{28}O_{13}$+H$^+$, 585.1609)

$^1$H NMR (DMSO-d6) δ1.97 (3H, s), 2.02 (9H, s), 4.11 (1H, br d, J=12.4), 4.19 (2H, dd, J=5.3, 12.4), 4.35 (1H, m), 5.01 (1H, t like, J=9.6), 5.10 (1H, dd J=7.9, 9.6), 5.39 (1H, t like, J=9.6), 5.76 (1H, d, J=7.9), 6.47 (1H, d, J=1.6), 6.84 (1H, d, =1.6), 7.08 (1H, s), 7.55-7.65 (3H, m), 8.09 (2H, d, J=7.9), 12.85 (1H, s, OH).

After the above obtained Chrycin 7-O-β-D-tetra-O—acetylglucopyranoside (0.23 g (0.39 mmol)) was added to 10 mL CH$_3$OH-Et$_3$N (2:1) and was refluxed with heating for 12 hr, it was concentrated and dried. The object (0.12 g (yield 72%)) was obtained by recrystallization of crude crystal from hexane-ethanol. The analytical values of the product (compound 5) are shown as follows.

FAB-MS: m/z 417 (M+H$^+$, 15%), 307 (32), 255 (34), 154 (100). FAB-HR-MS: m/z 417.1180 (calc. for $C_{21}H_{20}O_9$+H$^+$, 417.1182)

$^1$H NMR (DMSO-d$_6$) δ3.1-3.6 (5H, m), 3.70 (1H, m), 4.62 (1H, br s, OH), 5.08 (2H, d like, J=6.9, anomeric H, OH), 5.15 (1H, br s, OH), 5.43 (1H, br s, OH), 6.47 (1H, d, J=2.0), 6.87 (1H, d, J=2.0), 7.06 (1H, s), 7.45-7.70 (3H, m), 8.09 (2H, d, J=6.5), 12.72 (1H, br s, OH).

$^{13}$C NMR (DMSO-d$_6$) δ60.5, 69.5, 73.0, 76.4, 77.1, 94.9, 99.6, 99.7, 105.4, 105.5, 126.4, 129.0, 130.4, 132.1, 156.9, 160.9, 163.0, 163.5, 182.0.

SYNTHETIC EXAMPLES 2 AND 3

In the present synthetic example, compound 6 (apigenin 7-O-β-D-glucopyranoside) and compound 7 (apigenin 4', 7-di-O-β-D-glucopyranoside) were synthesized.

(1) Synthesis of apigenin 7-O-β-D-tetra-O-acetylglucopyranoside and apigenin 4', 7-di-O-β-D-tetra-O-acetylglucopyranoside.

According to the previous report (J. Chin. Chem. Soc., 48, 201-206 (2001)), apigenin was prepared by iodating naringenin (Tokyo Chemical Industry, Ltd.). Apigenin (1.66 g (6.1 mmol)), 3.59 g (9.2 mmol) of tetra-O-acetyl-α-D-glucopyranosilbromide (Kanto Chemical Co.) and 2.54 g (9.2 mmol) of Ag$_2$CO$_3$ were added to 30 mL of quinoline-pyridine (1:1) and stirred at room temperature for 1 hr. Furthermore, the above bromide (1.21 g (3.1 mmol)) and 0.83 g (3.0 mmol) of Ag$_2$CO$_3$ were added to the above mixture and subjected to further reaction for 8 hr. The reaction mixture was diluted in 50 mL of acetone and filtrated through Celite after stirring. After the residue obtained by concentration of the filtrate under reduced pressure was redissolved in 100 mL of ethylacetate, and shaken with 30 mL of 2N hydrochloric acid and then with saturated sodium chloride solution, the separated organic layer was dried (MgSO$_4$). The remainder obtained by concentration under reduced pressure was subjected silica gel column chromatography (chloroform:methanol=40:1 and chloroform:ethyl acetate=1:1) for two times. As the result, apigenin 7-O-β-D-tetra-O-acetylglucopyranoside (1.00 g (yield 27%)) and apigenin 4', 7-di-O-β-D-tetra-O-acetylglucopyranoside (0.21 g (yield 4%)) were obtained. The analytical value of the product is shown as follows.

(a) Apigenin 7-O-β-D-tetra-O-acetylglucopyranoside;

FAB-MS: m/z 601 (M+H$^+$, 30%), 331 (41), 271 (91), 169 (100). FAB-HR-MS: m/z 601.1541 (calc. for $C_{29}H_{28}O_{14}$+H$^+$, 601.1558)

$^1$H NMR (DMSO-d$_6$) δ1.97 (3H, s), 2.02 (9H, s), 4.11 (1, br d, J=12.5), 4.19 (1H, dd, J=5.3, 12.5), 4.33 (1H, m), 5.01 (1H, t like, J=9.7), 5.09 (2H, dd, J=6.9, 9.7), 5.39 (1H, 9.7), 5.74 (1H, d, J=7.9), 6.44 (1H, d, J=2.1), 6.79 (1H, d, J=2.1), 6.89 (1H, s), 6.92 (2H, d, J=8.7), 7.95 (2H, d, J=8.7), 13.02 (1H, s, OH).

(b) Apigenin 4', 7-di-O-β-D-tetra-O-acetylglucopyranoside;

FAB-MS: m/z 931 (M+H$^+$, 44%), 601 (33), 271 (66), 169 (49), 43 (100). FAB-HR-MS: m/z 931.2524 (calc. for $C_{43}H_{46}O_{23}$+H$^+$, 931.2508)

$^1$H NMR (DMSO-d$_6$) δ1.97 (6H, s), 2.01 (18H, s), 4.0-4.25 (4H, m), 4.25-4.37 (2H, m), 4.95-5.15 (4H, m), 5.3-5.5 (2H, m), 5.76 (2H, br d, J=7.9, anomeric H), 6.47 (1H, d, J=2.0), 6.83 (1H, d, J=2.0), 7.05 (1H, s), 7.17 (2H, d, J=8.9), 8.10 (2H, d, J=8.9), 12.91 (1H, s, OH).

(2) Synthesis of compound 6 (apigenin 7-O-β-D-glucopyranoside) and compound 7 (apigenin 4', 7-di-O-β-D-glucopyranoside)

Apigenin 7-O-β-D-tetra-O—acetylglucopyranoside (0.21 g (0.35 mmol)) as obtained above was added to 10 mL CH3OH-Et3N (2:1), refluxed with heating for 12 hr, and then concentrated and dried. The object (0.11 g) was obtained by recrystallization of obtained crude crystals from methanol (yield 73%).

Apigenin 4', 7-di-O-β-D-glucopyranoside (78 mg) was obtained from 0.17 g of apigenin 4', 7-di-O-β-D-tetra-O-acetylglucopyranoside as obtained above by the similar reaction (yield 71%). The analytical value of the product is shown as follows.

(c) Compound 6 (apigenin 7-O-β-D-glucopyranoside)

FAB-MS: m/z 433 (M+H$^+$, 9%), 241 (96), 185 (100). m/z 431 (M–H$^+$, 7%), 279 (20), 269 (24), 148 (100).

FAB-HR-MS: m/z 431.0993 (calc. for $C_{21}H_{20}O_{10}$—H$^+$, 431.0978)

MS (FAB$^+$): m/z 433 (M+H$^+$), 185, 150, 93, 75, 57, 45.

$^1$H NMR (DMSO-d$_6$) δ3.0-3.6 (5H, m), 3.70 (1H, dd, J=4.8, 9.4), 4.60 (1H, m, OH), 5.08 (2H, d like, J=5.1, anomeric H, OH), 5.13 (1H, d, J=4.5, OH), 5.39 (1H, d, J=4.5, OH), 6.43 (1H, d, J=2.1), 6.82 (1H, d, J=2.1), 6.89 (1H, s), 6.93 (2H, d, J=8.8), 7.95 (2H, d, J=8.8), 10.40 (1H, br s, OH), 12.95 (1H, s, OH).

$^{13}$C NMR (DMSO-d$_6$) δ60.6, 69.5, 73.0, 76.4, 77.1, 94.7, 99.4, 99.8, 103.0, 105.2, 115.9, 120.9, 128.5, 156.7, 160.9, 161.2, 162.7, 164.0, 181.8.

(d) Compound 7 (apigenin 4', 7-di-O-β-D-glucopyranoside)

FAB-MS: m/z 595 (M+H$^+$, 0.6%), 271 (4), 185 (56), 93 (100). FAB-HR-MS: m/z 595.1688 (calc. for $C_{27}H_{30}O_{15}$+H$^+$, 595.1663)

$^1$H NMR (DMSO-d$_6$) δ3.1-3.6 (10H, m), 3.70 (2H, m), 4.55-4.65 (2H, m, OH), 5.0-5.1 (4H, m, anomeric H ×2, OH ×2), 5.14 (2H, d like, J=4.0, OH), 5.35-5.45 (2H, m, OH), 6.44 (1H, d, J=2.1), 6.86 (1H, d, J=2.1), 6.99 (1H, s), 6.19 (2H, d, J=8.9), 8.06 (2H, d, J=8.9), 12.88 (1H, s, OH).

$^{13}$C NMR (DMSO-d$_6$) δ60.55, 60.60, 69.5, 69.6, 73.0, 73.1, 76.4, 76.5, 77.1, 94.8, 99.5, 99.7, 104.0, 105.3, 116.5, 123.5, 128.1, 156.8, 160.2, 160.9, 162.8, 163.4, 181.8.

SYNTHETIC EXAMPLE 4

In this synthetic example, compound 8 (rhoifoline, apigenin 7-O-β-neohesperidoside) was synthesized.

Naringin dihydrate (Tokyo Chemical Industry, Ltd., 1.23 g (2.0 mmol)) and 0.51 g (2.0 mmol) of iodide were added to pyridine (5 mL), and refluxed with heating for 9 hr under stirring. After the reactant was left to room temperature, insoluble matters were filtered off and the filtrate was concentrated under reduced pressure. The object (0.47 g) was got by crystallization of the obtained remainder from water containing ethanol (yield 41%). The analytical value of the product is shown as follows.

FAB-MS: m/z 579 (M+H$^+$, 10%), 277 (57), 241 (63), 207 (72), 185 (100). FAB-HR-MS: m/z 579.1712 (calc. for $C_{27}H_{30}O_{14}$+H$^+$, 579.1714)

$^1$H NMR (DMSO-d$_6$) δ1.19 (3H, d, J=6.1), 3.1-3.9 (9H, m), 4.47 (1H, d, J=4.4, OH), 4.6-4.75 (3H, m, OH ×3), 5.12 (1H, s, anomeric H), 5.16 (1H, d, J=4.4, OH), 5.22 (H, d, J=6.6, anomeric H), 5.34 (1H, d, J=4.4, OH), 6.36 (1H, br s), 6.78 (1H, br s), 6.86 (1H, s), 6.93 (2H, d, J=8.6), 7.93 (2H, d, J=8.6), 10.40 (1H, s, OH), 12.96 (1H, s, OH).

$^{13}$C NMR (DMSO-d$_6$) δ18.1, 60.4, 68.3, 69.6, 70.35, 70.43, 71.8, 76.2, 77.0, 77.1, 94.4, 97.7, 99.2, 100.4, 103.1, 105.3, 115.9, 120.9, 128.4, 156.8, 160.9, 161.2, 162.3, 164.0, 181.7.

EXAMPLE 2

The supercooling activities of flavonoid glycoside (the following compound 5 to 8, wherein the number in the formula represents the number of the compounds) synthesized in synthetic examples 1 to 4 were measured by the method similar to example 1, except that the concentration of the test compounds was 0.1 mg/mL.

[chemical formula 5]

5

6

7

8

Resultantly, the supercooling activity of compound 5 (Chricin-7-O-D-glucopyranoside), that of compound 6 (apigenin 7-O-D-glucopyranoside), that of compound 7 (apigenin 4', 7-di-O-D-glucopiranoside) and that of compound 8 (rhoifolin) are −4.5° C., −12.0° C., −4.9° C. and −1.8° C., respectively.

EXAMPLE 3

The storage liquid was prepared by adding 0.01% by weight of kaempferol-7-glucoside (compound 2 (Cj5)), Extrasynthese Co.) and 1% by volume of DMSO (Wako pure chemical industries Ltd., guaranteed reagent) to a buffer solution (UW liquid, 100 mM lactobionic acid, 25 mM KH2PO4, 5 mM MgSO$_4$, 30 mM raffinose, 2.5 mM adenosine, 3 mM GSH, 1 mM allopurinol, 0.25 mg/mL streptomycin, 10 UI/mL penicillin). Although, DMSO was used to enhance the solubility of kaempferol-7-O-glucoside, there was no effect on viability even for 4° C. storage sample (FIG. 8).

For comparison, a mixed solution (UW liquid) without kaempferol-7-O-glucoside and DMSO was prepared.

The viability of cells was evaluated by trypan blue (GIBCO) staining, when pig liver cells 5×106 cells/mL were dipped in 0.5 cc of the above storage liquid, supercooled at −5° C. and at −8° C., and stored for 1, 4 and 7 days.

Figure 8:
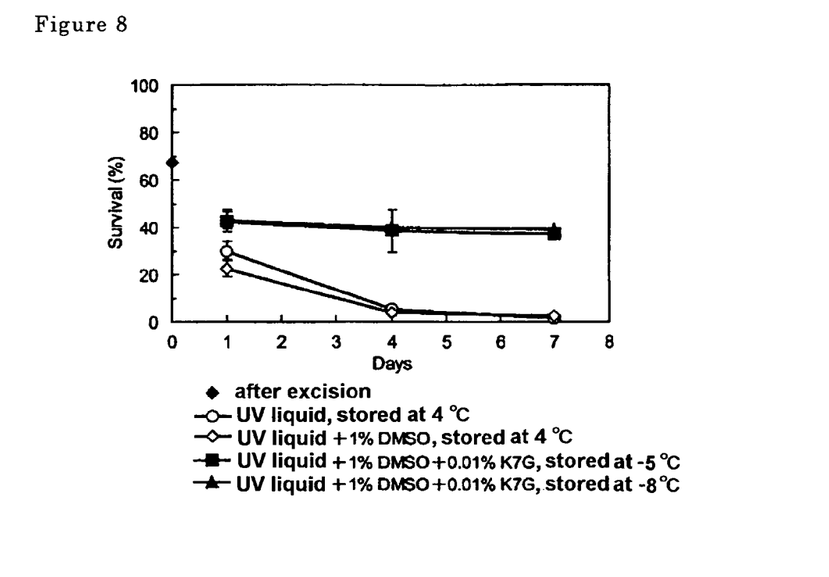
FIG. 8 shows the viability of cells, after pig liver fragments were stored in supercooling state, by dipped in the low temperature storage liquid (at −5° C. and at −8° C.) containing kaempferol-7-O-glucoside (K7G). The horizontal axis shows storage time (days) and the vertical axis shows viability (%).

The result is shown in FIG. 8. It was found that low temperature storage by supercooling induced by kaempferol-7-O-glucoside enables storage of viable animal cells for long-term.

EXAMPLE 4

As a vitrification liquid, 75% dilution solution of PVS2 liquid (22.5% by volume glycerol, 11.25% by volume of ethyleneglycol, 11.25% by volume of DMSO, 0.4 M sucrose, the remainder was Murashige & Skoog medium, DUCHEFA BIOCHEMIE BV) supplemented with 0.05% by weight of kaempferol-7-O-glucoside (compound 2, Extrasynthese Co.) was used (hereinafter referred to as "75% vitrification liquid"). Since viability of cranberry shoot apexes is lowered significantly with loading time by dipping in PVS2 liquid at room temperature due to chemical toxicity, the mixed solution with reduced content (75%) of vitrification liquid as described above was used.

For comparison, a mixed solution without kaempferol-7-O-glucoside was prepared. Shoot apexes (buds) are isolated from cranberry (subcultured in Hokkaido University, Graduate School of Agriculture) and dipped in the above mixed solution at room temperature.

Figure 9:
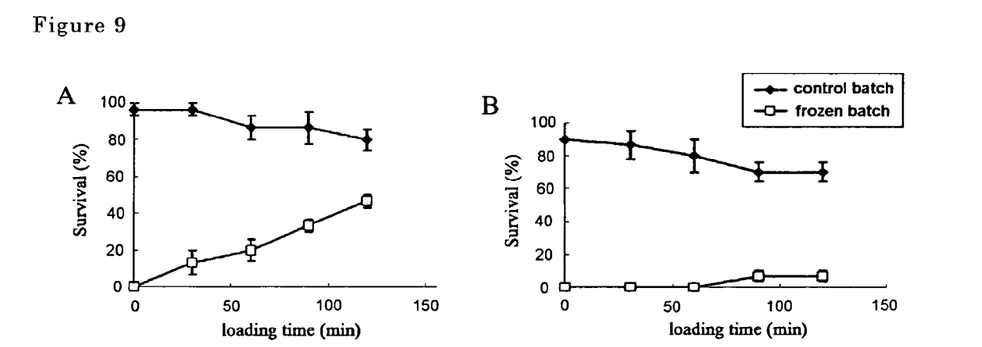
FIG. 9 shows the viability of cranberry shoot apexes (buds) stored in 75% vitrification liquid at room temperature for a specified loading time (control batch), and that of the above apexes dipped in liquid nitrogen after that and thawed to room temperature (frozen batch).

Since the concentration of vitrification liquid was reduced, viability of apexes as a function of loading time at room temperature was comparatively high in spite of the gradual decrease (control batches of FIG. 9A and FIG. 9B).

On the other hand, survival of shoot apexes, which were dipped in 75% vitrification liquid containing kaempferol-7-O-glucoside at room temperature for a specified loading time, put into liquid nitrogen, frozen for overnight, and then thawed at room temperature, is shown in frozen batch of FIG. 9A. Similarly, survival of the apexes, which were dipped in a vitrification liquid without kaempferol-7-O-glucoside and frozen, is shown in frozen batch of FIG. 9B.

The survival of apexes frozen in vitrification liquid without mixing kaempfrol-7-O-glucoside shows significant damage due to freezing (frozen batch of FIG. 9B).

Since addition of kaempferol-7-O-glucoside to vitrification liquid significantly reduced the damage due to freezing (frozen batch of FIG. 9A), it verified that supercooling storage was possible.

The vitrification storage of the biological materials such as cranberry shoot apexes has been impossible due to chemical toxicity of conventional vitrification liquid. However, addition of supercooling promoting agent of the present invention enabled to use as vitrification liquid even if the concentration of vitrification liquid was lowered down to the concentration, wherein the chemical toxicity is negligible, and enabled to store the biological materials in frozen state at extreme cold state without damage by chemical toxicity due to high concentration of vitrification liquid and by freezing.

What is claimed is:

1. An antifreezing liquid prepared by dissolving a supercooling promoting agent in water or in an aqueous solution containing additives, wherein the antifreezing liquid comprises equal to or more than 0.01 g/L of the supercooling promoting agent, and wherein the supercooling promoting agent comprises a flavonoid glycoside represented by the following general formula:

[Chemical Formula 1]

wherein
at least one of $X^1$ to $X^4$ is a sugar residue in which a hydrogen is removed from the hemiacetal hydroxyl group of monosaccharides or oligosaccharides and others are hydroxyl group or hydrogen atom; and
$R^1$ to $R^6$, which may be identical to or different from the other groups, are hydrogen atom, hydroxyl or methoxy group.

2. The antifreezing liquid of claim 1, further comprising 1 to 40% by volume of one or more cryoprotective agents.

3. The antifreezing liquid of claim 2, further comprising biological materials and cooled to a temperature between 0 and −15° C.

4. A composition comprising the antifreezing liquid of claim 2, further comprising biological materials, wherein the composition is cooled to a temperature between 0° C. and −15° C.

5. A vitrification liquid comprising equal to or more than 0.01 g/L of a supercooling promoting agent in a vitrification solution, wherein the vitrification solution comprises 20-100% by volume of one or more cryoprotective agents and the remainder is water or aqueous solution containing additives, and wherein the supercooling promoting agent comprises a flavonoid glycoside represented by Chemical Formula 1 wherein at least one of X to $X^4$ is a sugar residue in which a hydrogen is removed from the hemiacetal hydroxyl group of monosaccharides or oligosaccharides and others are hydroxyl group or hydrogen atom; and
$R^1$ to $R^6$, which may be identical to or different from the other groups, are hydrogen atom, hydroxyl or methoxy group.

6. The vitrification liquid of claim 5, comprising equal to or more than 40% by volume of the water or the aqueous solution containing additives.

7. The vitrification liquid of claim 6, further comprising biological materials and cooled to liquid nitrogen temperature.

8. A method of supercooling a sample of biological material comprising:
a) contacting at least 0.01 g/L of supercooling promoting agent with a sample of biological material, wherein the supercooling promoting agent comprises a flavonoid glycoside represented by Chemical Formula 1 wherein at least one of $X^1$ to $X^4$ is a sugar residue in which a hydrogen is removed from the hemiacetal hydroxyl group of monosaccharides or oligosaccharides and others are hydroxyl group or hydrogen atom; and
$R^1$ to $R^6$, which may be identical to or different from the other groups, are hydrogen atom, hydroxyl or methoxy group; and
b) cooling the sample at a rate of 0.2° C/minute to a temperature ranging from 5° C. to −15° C.

9. The method of claim 8, wherein $X^2$ is a sugar residue of glucose, mannose or galactose; and $X^1$, $X^3$ and $X^4$, which may be identical to or different from the other groups, are hydroxyl group or hydrogen atom; and $R^1$ to $R^6$ are hydrogen atoms.

10. A method of preparing an antifreezing liquid, the method comprising dissolving a supercooling promoting agent in water or in an aqueous solution containing additives, wherein the antifreezing liquid comprises at least 0.01 g/L of the supercooling promoting agent, and wherein the supercooling promoting agent comprises a flavonoid glycoside represented by Chemical Formula 1 wherein at least one of $X^1$ to $X^4$ is a sugar residue in which a hydrogen is removed from the hemiacetal hydroxyl group of monosaccharides or oligosaccharides and others are hydroxyl group or hydrogen atom; and $R^1$ to $R^6$, which may be identical to or different from the other groups, are hydrogen atom, hydroxyl or methoxy group.

11. The method of claim 10, wherein $X^2$ is a sugar residue of glucose, mannose or galactose; and $X^1$, $X^3$ and $X^4$, which may be identical to or different from the other groups, are hydroxyl group or hydrogen atom; and $R^1$ to $R^6$ are hydrogen atoms.

12. A method of preparing a vitrification liquid, the method comprising dissolving a supercooling promoting agent in a vitrification solution, wherein the vitrification solution comprises 20-100% by volume of one or more cryoprotective agents and the remainder is water or aqueous solution containing additives, and wherein the vitrification liquid comprises at least 0.01 g/L of the supercooling promoting agent, and wherein the supercooling promoting agent comprises a flavonoid glycoside represented by Chemical Formula 1 wherein at least one of $X^1$ to $X^4$ is a sugar residue in which a hydrogen is removed from the hemiacetal hydroxyl group of monosaccharides or oligosaccharides and others are hydroxyl group or hydrogen atom; and $R^1$ to $R^6$, which may be identical to or different from the other groups, are hydrogen atom, hydroxyl or methoxy group.

13. The method of claim 12 wherein $X^2$ is a sugar residue of glucose, mannose or galactose; and $X^1$, $X^3$ and $X^4$, which may be identical to or different from the other groups, are hydroxyl group or hydrogen atom; and $R^1$ to $R^6$ are hydrogen atoms.

* * * * *

UNITED STATES PATENT AND TRADEMARK OFFICE
CERTIFICATE OF CORRECTION

PATENT NO. : 7,837,895 B2  
APPLICATION NO. : 12/309332  
DATED : November 23, 2010  
INVENTOR(S) : Fujikawa et al.

Page 1 of 1

It is certified that error appears in the above-identified patent and that said Letters Patent is hereby corrected as shown below:

In column 16, line 26, change:

X to $X^4$ to $X^1$ to $X^4$

Signed and Sealed this
Eighth Day of February, 2011

David J. Kappos
*Director of the United States Patent and Trademark Office*